United States Patent [19]
Frank

[11] Patent Number: 5,092,186

[45] Date of Patent: Mar. 3, 1992

[54] MOTION CONVERTER FOR SMALL APPLIANCES DRIVEN BY AN ELECTRIC-MOTOR

[75] Inventor: Karlheinz Frank, Offenbach am Main, Fed. Rep. of Germany

[73] Assignee: Rowenta-Werke GmbH, Offenbach am Main, Fed. Rep. of Germany

[21] Appl. No.: 544,396

[22] Filed: Jun. 27, 1990

[30] Foreign Application Priority Data

Jun. 27, 1989 [DE] Fed. Rep. of Germany ....... 3920942

[51] Int. Cl.⁵ .................. F16H 21/16; F16H 25/08
[52] U.S. Cl. ............................................ 74/55; 74/25
[58] Field of Search ............... 74/55, 86; 128/62 A; 15/22.1, 110, 167.1; 30/43.3

[56] References Cited

U.S. PATENT DOCUMENTS

| | | | |
|---|---|---|---|
| 2,077,805 | 4/1937 | Muros | 30/43.3 |
| 2,342,467 | 2/1944 | Hagopian | 30/43.3 |
| 2,993,488 | 7/1961 | Stec | 74/55 X |
| 3,029,651 | 4/1962 | Flatt | 15/22.1 X |
| 3,524,088 | 8/1970 | Ryckman, Jr. | 74/55 |
| 4,320,777 | 3/1982 | Tomlin et al. | 74/55 X |
| 4,326,314 | 4/1982 | Moret et al. | 74/48 X |

FOREIGN PATENT DOCUMENTS

| | | | |
|---|---|---|---|
| 819981 | 11/1951 | Fed. Rep. of Germany | 74/86 |
| 3218596 | 11/1983 | Fed. Rep. of Germany | 15/22.1 |
| 43970 | 12/1960 | Poland | 74/55 |
| 750190 | 7/1980 | U.S.S.R. | 74/55 |
| 1279677 | 12/1986 | U.S.S.R. | 74/55 |
| 1287954 | 2/1987 | U.S.S.R. | 74/55 |

Primary Examiner—Allan D. Herrmann
Assistant Examiner—Julie Krolikowski
Attorney, Agent, or Firm—Toren, McGeady & Associates

[57] ABSTRACT

A motion converter for small appliances driven by electric motors, such as electric toothbrushes, electric razors or the like, comprising a motor, tool bit and tool bit carrier, which is driven by the rotary motion of the motor and imparts a preferably orbital motion to the tool bit. The latter is accomplished by a novel mechanism for converting the rotary motion of the motor shaft into a generally transverse reciprocating motion. The mechanism employs a follower having a guide slot with parallel side faces and conically extending, radial outer contoured surfaces. The follower comprises a bore for the motor shaft or for a cam on the motor shaft and is slidingly mounted thereon.

8 Claims, 2 Drawing Sheets 5,092,186

MOTION CONVERTER FOR SMALL APPLIANCES DRIVEN BY AN ELECTRIC-MOTOR

The invention is directed to a motion converter for small appliances driven by an electric motor, preferably electric toothbrushes, electric razors or the like, comprising a motor, tool bit and tool bit carrier, which is driven by the rotational motion of a motor and imparts a generally reciprocating or orbital motion to the tool bit connected with it.

BACKGROUND OF THE INVENTION

In case of electrically driven small appliances, especially with electrical toothbrushes, electrical razors or similar electrical small appliances, it was found to be advantageous if the rotational motion of the motor drive shaft is transposed by means of a motion converter into a reciprocating or oscillating output motion.

A species-like electrically driven toothbrush is known from DE-AS 11 95 267, where during operation the brush element performs a reciprocating and oscillating motion with the help of a motion converter. An electric razor (U.S. Pat. No. 2,077,805) is also known whose tool bit when in working position performs a rotary and oscillating motion.

The known devices have the disadvantage that the motion converter is difficult to fabricate and install, since the space requirement within the appliance is very large and thus no handy, smaller size appliances can be fabricated if they are equipped with one of the known motion converters.

SUMMARY OF THE INVENTION

It is the object of this invention to create a motion converter for a small appliance driven by electric motors, which does not have the disadvantages of the known devices, is easy to manufacture and to install and requires only little space, whereby small, space-saving and handy appliances can be manufactured.

This object is achieved in accordance with a feature of the invention by providing a generally cylindrical cam member which is eccentrically mounted on the motor shaft, and cooperates with a follower in such manner that the follower end is forced to move in a direction transverse to the motor shaft axis. The tool to be driven is connected to or carried by the follower end.

In an alternative embodiment in accordance with the invention, the cam member may be omitted by offsetting the motor shaft so that during rotation it follows an eccentric orbit.

In a preferred embodiment, the drive motor is in operational connection with the tool bit carrier by means of a cylindrically-shaped cam. The cam is provided with a bore for securing same to the motor shaft. The cam follower is detachably mounted on the cam. The follower, connected to the tool bit carrier, comprises a guide slot with parallel side faces and conically extending radial outer contoured area surfaces. The cam is guided in the guide slot. The longitudinal axes of the cam and its bore define an angle of less than 90°. The stated features achieve that, during operation, the tool bit connected with the tool carrier performs an orbital motion. Thus, the motion converter in the invention can advantageously be used in electric tooth brushes, since the motion converter only requires very little space and thus a very handy tool can be fabricated, which approaches very closely to the handling of a conventional tooth brush. The motion converter in the invention can also be used to advantage in electric razors or electric shoeshine appliances, since these appliances can also be designed to have extraordinarily small dimensions, while having a high efficiency and with the orbital motions of the tool bits they provide excellent shaving or shoeshine results.

BRIEF DESCRIPTION OF THE DRAWINGS

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

In the drawings.

DETAILED DESCRIPTION OF THE PREFERRED EMBODIMENTS

Figure 2:
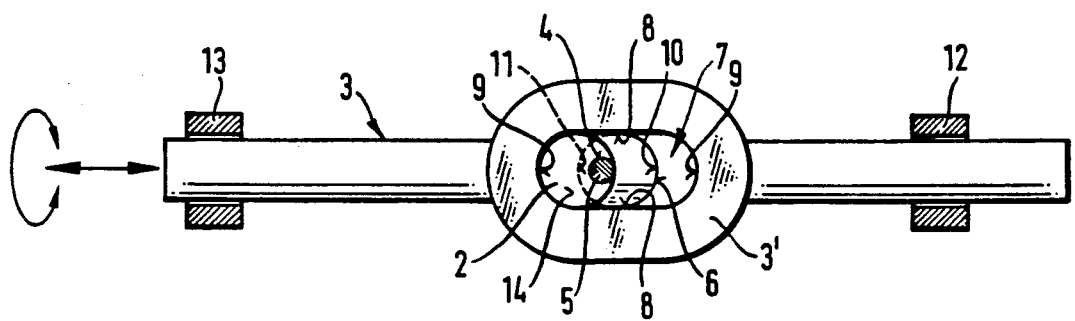
FIG. 2 is a view of the motion converter of FIG. 1 along the line B—B, viewed from below.
Figure 1:
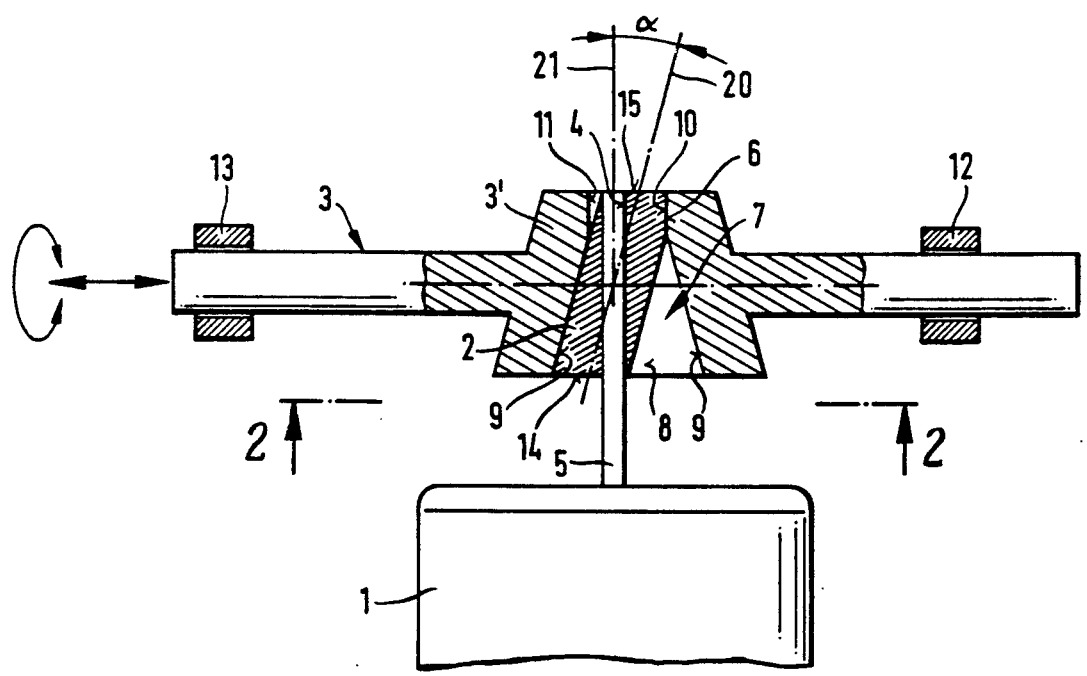
FIG. 1 is a cross-section of one form of motion converter in accordance with the invention.

The motion converter depicted in FIGS. 1 and 2 comprises an electric motor 1, which is in operational connection by means of a cam 2 with a tool bit carrier 3 having an integral follower part 3'. The cam 2 is substantially cylindrical with a longitudinal axis 20, and has a bore 4 for receiving the motor shaft 5. The concentric longitudinal axes 21 of the bore 4 and shaft 5, and that 20 of the cam 2 enclose an angle "α" <90°. A preferred angle is about 5° to 30°. A surface 6, provided at the outer wall of the cam 2, extends parallel to the bore 4. In the follower 3', a guide slot 7 for the cam 2 is provided. The guide slot 7 has at its outer remote end parallel side walls 8 joined to conically extending radial outer contoured area surfaces 9 forming a generally oval shape, at the outer boundary of the follower 3'. Surfaces 10 and 11 are provided at the contoured area surfaces 9, which during operation come into operational engagement with the face 6 of the cam 2. The cam end surfaces 14, 15 form planes perpendicular to the bore axis 21.

In the motion converter shown, the transversely extending ends of tool bit carrier 3 are retained in bearings 12 and 13, the cam 2 is locked, as by keying, to the shaft 5, and the follower 3 is detachably slid upon the cam 2 via widened opening 23 at the bottom or inner boundary of the follower 3'. In operation, the cam 2 is driven in a rotary motion about the bore axis 21. Its eccentric mounting and configuration causes its surfaces to follow a generally transverse motion (horizontal in FIG. 1). As a result of the novel configuration of the slot 7 in the carrier 3, the tool carrier ends not only reciprocate but also pivot, producing an orbital motion, shown by the arrows. The motion converter in the invention can be used advantageously in electric razors and electric toothbrushes, wherein for instance, in case the object of the invention is used in electric toothbrushes, the tool bit carrier 3 is configured as a brush adapter or holder and is in operational connection by means of the cylindrical cam 2 with the drive motor; meaning, that during the operation, the cylindrical cam driven by the motor shaft 5 can by means of its contoured surface and the face 6 be brought into engagement with the inner wall of the guide slot 7 and the faces 10 and 11 formed at the radial contoured surfaces 9. Thus, the brush adapter will perform a reciprocal and a rotary motion, meaning an orbital motion. This brush motion is eminently suitable for brushing teeth. A very handy and easily assemblable electric toothbrush can be manufactured by employing the motion converter of the invention.

Figure 3:
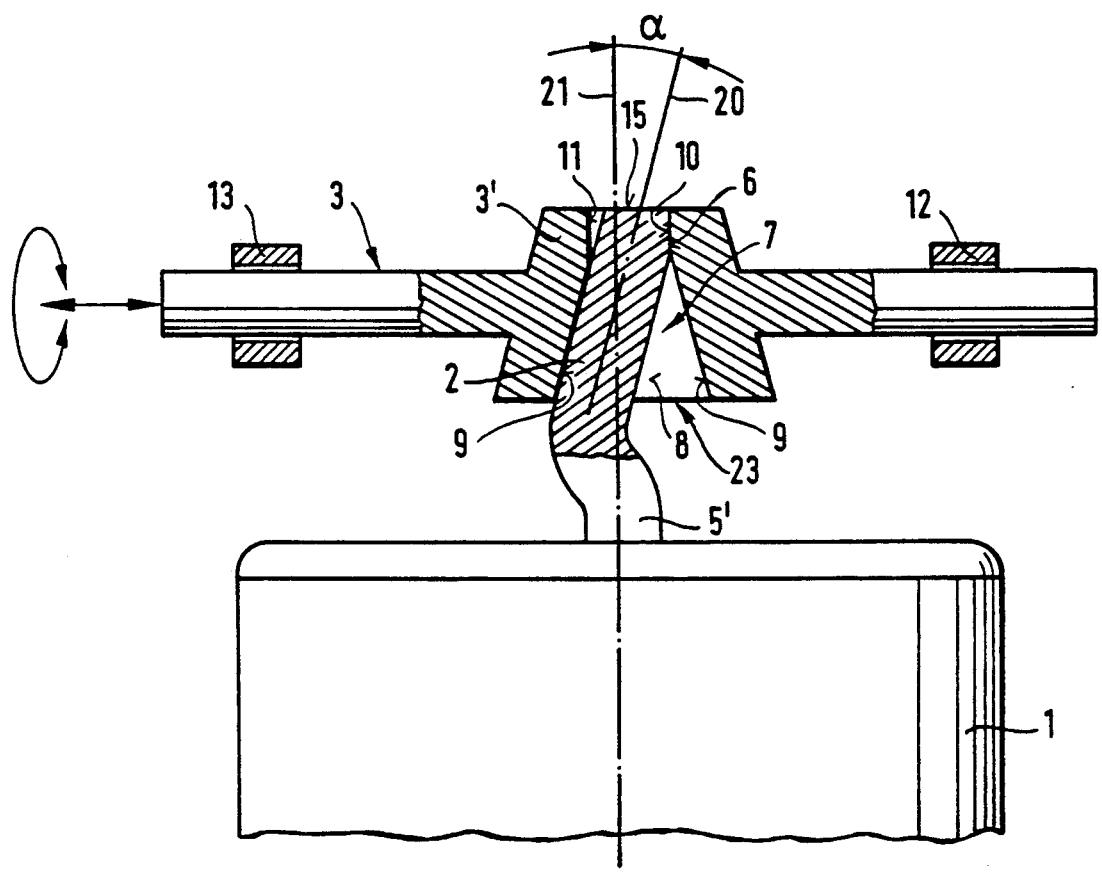
FIG. 3 is a view similar to FIG. 1 of an alternative embodiment.

In the embodiment disclosed in FIGS. 1 and 2, the cam member 2 is locked to the motor shaft 5, which is centered with respect to the motor housing 1. As a result, the cam member 2, due to its tilted longitudinal axis 20 with respect to the motor shaft 21 (which is centered with respect to the motor housing), is compelled to follow an eccentric rotary path, which drives the follower member 3' in its horizontal reciprocating path. As an alternative embodiment, if the motor shaft 5 is offset with respect to the motor 1 axis, then the cam member 2 can be omitted, and the motor shaft 5 would then be driven in an eccentric path and could then act directly as a cam causing the follower member 3' to follow the desired horizontal reciprocating path. This alternative embodiment is illustrated in FIG. 3. In FIG. 3, the same reference numerals are used for corresponding elements. The modified elements for this embodiment include the offset motor shaft 5'. The operation is otherwise similar to what was described earlier in connection with the FIGS. 1 and 2 embodiment.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A mechanism for converting rotary motion into generally reciprocating motion, comprising:

a generally cylindrical cam member having a longitudinal axis and having an eccentric bore extending lengthwise of the member and whose bore axis defines an angle α with the said longitudinal axis of less than 90°, said bore being adapted to receive a motor shaft whereby the cam member when connected to the motor shaft can be caused to rotate about said bore axis, a follower member having a guide slot for receiving the cam member and removably seated on the cam member, said guide slot having at one boundary of the follower member a generally oval-shaped opening formed by parallel side faces and interconnecting contoured end surfaces extending through said follower member, said guide slot having at its opposite boundary a widened opening such that the spacing between end surfaces at said opposite boundary is larger than the spacing between end surfaces at said one boundary.

2. A mechanism as claimed in claim 1, wherein the cam member and the guide slot are configured such that in one position the cam member engages with one end surface at the widened opening on said opposite boundary and engages with an opposite end surface at the oval-shaped opening on said one boundary.

3. In combination, a motor having a shaft that can be rotated; means coupled to the shaft for converting its rotary motion into substantially reciprocating motion, and converting means comprising:

a generally cylindrical cam member having a longitudinal axis and having an eccentric bore extending generally lengthwise of the member and whose bore axis defines an angle α with the said longitudinal axis of less than 90°, said cam member being mounted via said bore on said motor shaft whereby when the motor is energized the cam member can be caused to rotate about said bore axis, a follower member having a guide slot for receiving the cam member and removably seated on the cam member, said guide slot having at one boundary a generally oval-shaped opening formed by parallel side faces and interconnecting contoured end surfaces extending through said follower member, said guide slot having at its opposite boundary a widened opening such that the spacing between end surfaces at said opposite boundary is larger than the spacing between end surfaces at said one boundary.

4. The combination as claimed in claim 3, wherein the cam member and the guide slot are configured such that in one position cam member engages with one end surface at the widened opening on said opposite boundary and engages with an opposite end surface at the oval-shaped opening on said one boundary.

5. The combination of claim 4, wherein the cam member at its end remote from the motor has a generally semi-cylindrically-shaped surface complementing the end surfaces at the outer one boundary, said semi-cylindrically-shaped surface and the complementary end surfaces all extending substantially parallel to the motor shaft.

6. The combination of claim 4, wherein the cam member boundaries are substantially parallel planes extending substantially perpendicular to the bore.

7. The combination of claim 4, wherein said follower member has an integral elongated part extending generally transverse to the bore axis, and bearing means supporting said elongated part for generally reciprocating motion in said transverse direction.

8. In combination, a motor having an offset-mounted shaft that can be rotated in an orbital path; means coupled to the shaft for converting its rotary motion into substantially reciprocating motion, said converting means comprising:

a follower member having a guide slot for receiving the offset shaft and removably seated on the offset shaft, said guide slot having at one boundary of the follower member a generally oval-shaped opening formed by parallel side faces and interconnecting contoured end surfaces extending through said follower member, said guide slot having at its opposite boundary a widened opening such that the spacing between end surfaces at said opposite boundary is larger than the spacing between end surfaces at said one boundary, whereby when the offset shaft is rotated, it follows an orbital path causing the follower member to perform a generally reciprocating motion.

* * * * *